United States Patent [19]

Matsumoto et al.

[11] 4,345,102

[45] Aug. 17, 1982

[54] PROCESS FOR PRODUCING ETHYLENE GLYCOL MONO-T-BUTYL ETHER

[75] Inventors: Tadashi Matsumoto; Osamu Kuratani; Yasunori Hirose, all of Soka; Susumu Toba, Saitama, all of Japan

[73] Assignee: Maruzen Oil Co., Ltd., Osaka, Japan

[21] Appl. No.: 156,136

[22] Filed: Jun. 3, 1980

Related U.S. Application Data

[63] Continuation-in-part of Ser. No. 70,761, Aug. 30, 1979, abandoned.

[30] Foreign Application Priority Data

Aug. 30, 1978 [JP] Japan .................................. 53-105814

[51] Int. Cl.$^3$ ............................................. C07C 41/06
[52] U.S. Cl. .................................................... 568/678
[58] Field of Search ........................ 568/678, 671, 697

[56] References Cited

U.S. PATENT DOCUMENTS 2,480,940 9/1949 Leum et al. ......................... 568/697

FOREIGN PATENT DOCUMENTS 2450667 4/1975 Fed. Rep. of Germany ...... 568/678
51-29413 3/1976 Japan .................................. 568/678
957000 4/1964 United Kingdom ............... 568/647

Primary Examiner—Howard T. Mars
Attorney, Agent, or Firm—Sughrue, Mion, Zinn, Macpeak & Seas

[57] ABSTRACT

Ethylene glycol mono-t-butyl ether is produced by contacting a starting mixture of feed materials comprising ethylene glycol di-t-butyl ether and ethylene glycol with a strongly acidic cation-exchange material, thereby to react said ethylene glycol and ethylene glycol di-t-butyl ether to produce ethylene glycol mono-t-butyl ether; the reaction is carried out at about 30° to 130° C. under an atmospheric pressure or an increased pressure; the molar ratio of the feed ethylene glycol to the feed ethylene glycol di-t-butyl ether is about 1:0.01 to 1:20; the feed material may be a mixture comprising ethylene glycol di-t-butyl ether, ethylene glycol and at least one member selected from the group consisting of ethylene glycol mono-t-butyl ether, diisobutylene, and triisobutylene; also the reaction can be carried out by either a batch process or a continuous flowing process.

15 Claims, No Drawings

PROCESS FOR PRODUCING ETHYLENE GLYCOL MONO-T-BUTYL ETHER

RELATED APPLICATIONS

This application is a continuation-in-part of U.S. Application Ser. No. 70,761, filed Aug. 30, 1979 now abandoned.

BACKGROUND OF THE INVENTION

1. Field of the Invention

The present invention relates to a process for producing ethylene glycol mono-t-butyl ether and, particularly, to a process for converting ethylene glycol di-t-butyl ether into ethylene glycol mono-t-butyl ether.

2. Description of the Prior Art

Ethylene glycol mono-t-butyl ether is a useful substance having excellent properties as a solvent, a dispersing agent or a diluent in the field of coatings or inks, etc. It has been well known that ethylene glycol mono-t-butyl ether can be synthesized from isobutylene and ethylene glycol in the presence of an acid catalyst. It has been further described in the U.S. Pat. Nos. 3,317,483, 3,170,000, and 2,480,940 that, in this case, strongly acidic cation-exchange materials are useful as the catalyst. However, in producing ethylene glycol mono-t-butyl ether from isobutylene and ethylene glycol, it is not possible to avoid by-producing ethylene glycol di-t-butyl ether, even if a catalyst is used. If the ethylene glycol di-t-butyl ether is by-produced, the yield of ethylene glycol mono-t-butyl ether is reduced and this detracts from the economic value of its production. Accordingly, if it were possible to convert the by-produced ethylene glycol di-t-butyl ether into the desired ethylene glycol mono-t-butyl ether, remarkable advantages would be obtained. However, a good process for converting ethylene glycol di-t-butyl ether into ethylene glycol mono-t-butyl ether has not been known.

SUMMARY OF THE INVENTION

A principal object of the present invention is to produce ethylene glycol mono-t-butyl ether from ethylene glycol di-t-butyl ether.

Another object of the present invention is to produce ethylene glycol mono-t-butyl ether in a high yield from ethylene glycol di-t-butyl ether.

A further object of the present invention is to provide a process for producing ethylene glycol mono-t-butyl ether by an easy operation.

A further another object of the present invention is to provide a process for converting ethylene glycol di-t-butyl ether which is by-produced upon production of ethylene glycol mono-t-butyl ether from isobutylene and ethylene glycol into the useful ethylene glycol mono-t-butyl ether.

A process to which the present invention is applied is a process for producing ethylene glycol mono-t-butyl ether. According to the present invention, the ethylene glycol mono-t-butyl ether is produced by a process which comprises a step of contacting a starting mixture comprising ethylene glycol di-t-butyl ether and ethylene glycol with a strongly acidic cation-exchange material, thereby to react said ethylene glycol with said ethylene glycol di-t-butyl ether to produce ethylene glycol mono-t-butyl ether.

DETAILED DESCRIPTION OF THE INVENTION

In the conventional processes of producing ethylene glycol mono-t-butyl ether (MBE) by using isobutylene and ethylene glycol as starting materials, the amount of ethylene glycol di-t-butyl ether (DBE) formed as a by-product increases with passage of the reaction time and is not decreased. The present invention is based on the finding that MBE can be produced from DBE and ethylene glycol as starting materials. That is, the present invention is characterized in that DBE is present as the starting material in the reaction system when the reaction is initiated, i.e., the present invention is achieved by adding DBE other than DBE formed automatically as by-product in accordance with the specific reaction of isobutylene and ethylene glycol in the prior art systems.

Though the processes of the present invention is suitable for converting ethylene glycol di-t-butyl ether which is formed as a by-product in the production of ethylene glycol mono-t-butyl ether from ethylene glcyol and isobutylene, into ethylene glycol mono-t-butyl ether, the ethylene glycol di-t-butyl ether used in the present invention is not necessarily limited to that produced by the reaction of isobutylene and ethylene glycol, and that produced from other raw materials and by other reactions may be used.

Further, the reaction in the present invention is not substantially interfered with if the product, by-products and additives in the reaction of producing ethylene glycol mono-t-butyl ether from isobutylene and ethylene glycol, such as diisobutylene, triisobutylene, and ethylene glycol mono-t-butyl ether, etc., are present. The process for producing ethylene glycol mono-t-butyl ether from ethylene glycol and isobutylene itself is disclosed in, for example, U.S. Pat. Nos. 3,170,000, 3,317,483 and 2,480,940, which comprises reacting ethylene glycol with isobutylene in the presence of a strongly acidic cation-exchange material as a catalyst. Generally, a preferred molar ratio of the feed ethylene glycol to the feed isobutylene is about 1:0.05 to 1:20 in these processes. A preferred reaction temperature is about 20° to 130° C. and particularly 40° to 130° C. Though the reaction pressure may be either atmospheric pressure or an applied pressure, a pressure of about 1 to 50 Kg/cm$^2$ is preferred. The reaction may be carried out by either a batch or a continuous process. The resulting reaction mixture comprises isobutylene, diisobutylene, triisobutylene, ethylene glycol, ethylene glycol mono-t-butyl ether, ethylene glycol di-t-butyl ether, and the catalyst.

As the starting material of the present invention, ethylene glycol di-t-butyl ether which contains ethylene glycol mono-t-butyl ether may be used, because it is generally easier to separate ethylene glycol di-t-butyl ether and ethylene glycol mono-t-butyl ether as a mixture from the above described reaction mixture by distillation than to separate only the by-produced ethylene glycol di-t-butyl ether, since the ethylene glycol mono-t-butyl ether and the ethylene glycol di-t-butyl ether form an azeotropic mixture. Further, since the product obtained by removing isobutylene from the above described reaction mixture and then removing a part or all of the ethylene glycol mono-t-butyl ether is composed mainly of ethylene glycol di-t-butyl ether, it is possible to carry out the reaction according to the present invention by adding ethylene glycol or the catalyst (if the catalyst present or ethylene glycol present is insufficient) to convert, the ethylene glycol di-t-butyl ether into ethylene glycol mono-t-butyl ether by reacting with ethylene glycol.

As described above, the feed materials contacted with the catalyst in the process of the present invention may be any of a mixture of ethylene glycol and ethylene glycol di-t-butyl ether or a mixture comprising at least one member selected from ethylene glycol mono-t-butyl ether, diisobutylene and triisobutylene besides ethylene glycol di-t-butyl ether and ethylene glycol, and, particularly, a mixture of ethylene glycol, ethylene glycol di-t-butyl ether and ethylene glycol mono-t-butyl ether. Amounts of diisobutylene and triisobutylene are each at most about 10% by weight and generally about 3% by weight or less in the feed materials. These materials do not interfere significantly with the conversion of ethylene glycol di-t-butyl ether into ethylene glycol mono-t-butyl ether.

Further, in the reaction according to the present invention, the composition of the reaction product varies in accordance with the reaction temperature. Particularly, at temperatures higher than 50° C., it is preferred to limit the amount of the mono-ether in the feed materials, because if the ethylene glycol mono-t-butyl ether is present in a large amount in the feed materials, conversion of the diether into the mono-ether is prevented.

In the present invention, the strongly acidic cation-exchange materials used as the catalyst are, those which show strong acidity and are water-insoluble, namely, sulfonated materials having sulfonic acid groups ($SO_3H$) as functional groups. As the strongly acid cation-exchange materials, there are styrene sulfonic acid type cation-exchange resins, phenol sulfonic acid type cation-exchange resins, sulfonated asphalt and sulfonated coals, etc. The styrene sulfonic acid type cation-exchange resins are those which are prepared by sulfonating resins composed of a copolymer of styrene and an unsaturated polyene compound such as divinylbenzene (which are available as Amberlyst 15, Amerlite IR-118 and Amberlite IR-120 Manufactured by Rohm & Haas Co. and Dowex 50W-X12 manufactured by Dow Chemical Co., etc.). The phenol sulfonic acid type cation-exchange resins are those which are prepared by condensing phenolsulfonic acid with formaldehyde (which are available as Amberlite IR-1, Amberlite IR-100 and Amberlite IR-105G manufactured by Rohm & Haas Co., etc.). The sulfonated coals are those produced by sulfonating bituminous coal with sulfuric acid (which are available as Nalcite X and Nalcite AX manufactured by Dow Chemical Co. and Zeo-Karb H manufactured by the Permutit Co., Ltd., and Dusarit S manufactured by Acivit N.V., etc.). In case that these strongly acidic cation-exchange materials are available as neutral materials such as the sodium salts, they should be activated by processing with a strong inorganic acid such as hydrochloric acid and washing with water prior to using to remove sodium and chloride ions. Further, as the physical structure of these cation-exchange materials, any of gel type and macroporous type materials may be used. A preferred total exchange capacity range of these strongly acidic cation-exchange materials is at least about 0.5 meq/g-dry material and particularly about 1.0-7.0 meq/g-dry material.

If the reaction temperature is too low, the reaction rate is too slow. On the other hand, if it is too high, the ion-exchange material catalyst can suffer thermal damage. Accordingly a preferred temperature range is about 30° to 130° C. and particularly about 50° to 100° C. The reaction pressure is not particularly restricted, and the reaction can be carried out under atmospheric pressure or an applied pressure. Generally, a pressure sufficient to keep the reaction mixture at a liquid state is preferred, but a pressure under which a part of the reaction mixture exists as a gas may be used. A conveniently adopted pressure is about 1 to 50 kg/cm$^2$.

Though the molar ratio of ethylene glycol to ethylene glycol di-t-butyl ether is not particularly restricted, an excess of ethylene glycol is generally used. However, when it is not desired to have ethylene glycol in the product during separation and purification of the product, excess di-ether is used. Accordingly, the molar ratio of the feed ethylene glycol to the feed ethylene glycol di-t-butyl ether is generally in a range of about 1:0.01 to 1:20 and preferably about 1:0.05 to 1:10.

In case that a mixture comprising ethylene glycol mono-t-butyl ether is used as the feed material, the molar ratio of ethylene glycol di-t-butyl ether to ethylene glycol mono-t-butyl ether in the feed material is generally in a range of about 1:0 to 1:20, preferably about 1:0 to 1:10 and particularly about 1:0 to 1:5. In case that the reaction temperature is high as described above, for example, 50° C. or more, it is particularly preferred that the molar ratio of the di-ether to the mono-ether in the raw material is in a range of about 1:0 to 1:3, because conversion of the di-ether into the mono-ether is obstructed if the mono-ether is present in a large amount in the feed material. Though the amount of the cation-exchange material used as the catalyst is not necessarily limited, it is generally preferred in a range of about 0.5 to 30% and particularly 1 to 15% by weight based on the starting material. Further, though a solvent is not generally necessary, inert solvents, such as hydrocarbons exemplified by n-heptane, n-hexane, benzene, toluene, xylene, or halogenated hydrocarbons exemplified by trichloroethylene, tetrachloroethane may be used.

The reaction can be carried out by any of an agitation type batch process and a continuous process and can also be carried out in a fixed-bed flowing process. Though the reaction time is not restricted, it is preferably in a range of about 5 minutes to 50 hours and particularly about 20 minutes to 10 hours, in the case of the batch process. In case of the continuous process, it is preferred that liquid hourly space velocity of the starting material is about 0.1 to 10 hr$^{-1}$ and particularly 0.5 to 2 hr$^{-1}$. In case of the flowing process, it is preferred that linear velocity of all starting materials passing through the catalyst bed (flow amount of the materials cm$^3$/hr based on 1 cm$^2$ of the section area of the reactor, which is represented as a liquid state at a room temperature under an increased pressure) is about 30 cm/hr, or more and particularly about 60 cm/hr to 50 m/hr.

The separation of ethylene glycol mono-t-butyl ether from the reaction product can be carried out by a conventional method such as distillation and/or solvent extraction using a solvent such as water, heptane or alcohol, etc. or an extractive distillation method, etc.

According to the process of the present invention, it is possible to convert ethylene glycol di-t-butyl ether into ethylene glycol mono-t-butyl ether. Though the reaction mechanism of this reaction has not been established ethylene glycol mono-t-butyl ether is obtained in a good yield under mild conditions. Further, since the strongly acidic cation-exchange materials used as the catalyst have a low corrosion property as compared with sulfuric acid, it is unnecessary to line the reactor or conduits with expensive anticorrosion materials. Further, since the catalytic ion-exchange material is solid, separation of it from the reaction product is easily carried out and the reaction operation is simple.

It is particularly preferred to apply the process of the present invention to conversion of ethylene glycol di-t-butyl ether which is a by-product of the production of ethylene glycol mono-t-butyl ether from isobutylene and ethylene glycol, because the yield of useful ethylene glycol mono-t-butyl ether is very high. Accordingly the feed material may also contain ethylene glycol, ethylene glycol mono-t-butyl ether, diisobutylene, and triisobutylene.

The process of the present invention is illustrated in detail with reference to the following examples. However, the process of the present invention is not to be construed as limited to these examples.

EXAMPLE 1

In a stainless steel autoclave having a volume of 100 ml equipped with a stirrer, 5.2 g of a styrene sulfonic acid type strongly acid cation-exchange resin (Amberlyst 15, manufactured by Rohm & Haas Co., macroporous type resin, total exchange capacity: 4.9 meq/g-dry resin, specific surface area: 40–50 $m^2/g$, average pore size: 200–600 Å), 0.565 mols of ethylene glycol and 0.057 mols of ethylene glycol di-t-butyl ether were introduced and a nitrogen gas was introduced thereto. The mixture was subjected to reaction at 75° C. for 2 hours. The pressure was 20 $Kg/cm^2$. When the liquid reaction product was analyzed, it was ascertained that the product comprised 0.520 mols of ethylene glycol, 0.004 mols of diisobutylene, 0.004 mols of ethylene glycol di-t-butyl ether and 0.098 mols of ethylene glycol mono-t-butyl ether. The result is shown in Table 1. Ethylene glycol di-t-butyl ether was converted into ethylene glycol mono-t-butyl ether in a good yield.

EXAMPLE 2

In an autoclave having a volume of 100 ml equipped with a stirrer, 5.5 g of a styrene sulfonic acid type strongly acid cation-exchange resin (Amberlyst 15), 0.590 mols of ethylene glycol, 0.055 mols of ethylene glycol di-t-butyl ether and 0.064 mols of ethylene glycol mono-t-butyl ether were put, and nitrogen gas was introduced thereto. The mixture was subjected to reaction at 90° C. for 2 hours. The pressure was 20 $Kg/cm^2$. The liquid reaction product was analyzed and it was ascertained that the product comprised 0.565 mols of ethylene glycol, 0.013 mols of diisobutylene, 0.008 mols of ethylene glycol di-t-butyl ether and 0.136 mols of ethylene glycol mono-t-butyl ether. The result is shown in Table 1. In this reaction condition, the ethylene glycol di-t-butyl ether was converted into ethylene glycol mono-t-butyl ether notwithstanding ethylene glycol mono-t-butyl ether was contained in the feed material.

EXAMPLES 3 AND 4

A reaction of ethylene glycol with ethylene glycol di-t-butyl ether was carried out according to Example 1. The catalyst used was the styrene sulfonic acid type strongly acid cation-exchange resin: Amberlite IR-118 (manufactured by Rohm & Haas Co., gel type resin, total exchange capacity: 4.4 meq/g-dry resin, specific surface area: 1 $m^2/g$ or less) in Example 3 and the styrene sulfonic acid type strongly acid cation-exchange resin: Dowex 50 W-X12 (manufactured by Dow Chemical Co., gel type resin, total exchange capacity: 5.0 meq/g-dry resin, specific surface area: 1 $m^2/g$ or less) in Example 4. Reaction conditions and results are shown in Table 1.

TABLE 1

| Composition | Example 1 Reaction temperature and time 75° C., 2 hr | | | Example 2 Reaction temperature and time 90° C., 2 hr | | | Example 3 Reaction temperature and time 60° C., 4 hr | | | Example 4 Reaction temperature and time 50° C., 4 hr | | |
|---|---|---|---|---|---|---|---|---|---|---|---|---|
| | Feed material (mol) | Product (mol) | (Product) - (Feed material) (mol) | Feed material (mol) | Product (mol) | (Product) - (Feed material) (mol) | Feed material (mol) | Product (mol) | (Product) - (Feed material) (mol) | Feed material (mol) | Product (mol) | (Product) - (Feed material) (mol) |
| Ethylene glycol | 0.565 | 0.520 | −0.045 | 0.590 | 0.565 | −0.025 | 0.565 | 0.524 | −0.041 | 0.565 | 0.500 | −0.065 |
| Diisobutylene | 0 | 0.004 | 0.004 | 0 | 0.013 | 0.013 | 0 | 0.006 | 0.006 | 0 | 0.010 | 0.010 |
| DBE | 0.057 | 0.004 | −0.053 | 0.055 | 0.008 | −0.047 | 0.057 | 0.004 | −0.053 | 0.104 | 0.019 | −0.085 |
| MBE | 0 | 0.098 | 0.098 | 0.064 | 0.136 | 0.072 | 0 | 0.094 | 0.094 | 0 | 0.150 | 0.150 |

(Note)
DBE: Ethylene glycol di-t-butyl ether
MBE: Ethylene glycol mono-t-butyl ether

EXAMPLE 5

A strongly acid cation-exchange resin (Amberlyst 15) was previously swollen in ethylene glycol, 100 ml of which was put in a stainless steel reaction tube having a 10 mm inside diameter. After the reaction tube was heated to 75° C., 1.500 mols/hr of ethylene glycol and 0.160 mols/hr of ethylene glycol di-t-butyl ether were introduced by means of a micropump to carry out the reaction at 75° C. The linear velocity of the whole feed materials was about 150 cm/hr. Further, the pressure of the reaction system was kept so as to be 20 $Kg/m^2$. When a liquid reaction product which was produced after 5 to 6 hours from beginning of the reaction, at which the state of the reaction was normal, was analyzed, the results shown in the following table were obtained. The ethylene glycol di-t-butyl ether was effectively converted into ethylene glycol mono-t-butyl ether.

TABLE 2

| | Feed material Component (mol/hr) | Product Component (mol/hr) | (Product) - (Feed material) Component (mol/hr) |
|---|---|---|---|
| Ethylene glycol | 1.500 | 1.381 | −0.119 |
| Diisobutylene | 0 | 0.011 | 0.011 |
| DBE | 0.160 | 0.019 | −0.141 |

TABLE 2-continued

| | Feed material Component (mol/hr) | Product Component (mol/hr) | (Product) - (Feed material) Component (mol/hr) |
|---|---|---|---|
| MBE | 0 | 0.260 | 0.260 |

(Note)
DBE: Ethylene glycol di-t-butyl ether
MBE: Ethylene glycol mono-t-butyl ether

EXAMPLE 6

The reaction was carried out by the same manner as in Example 1 except that a mixture comprising 0.220 mols of ethylene glycol mono-t-butyl ether and small amounts of diisobutylene, and triisobutylene besides 0.590 mols of ethylene glycol and 0.055 mols of ethylene glycol di-t-butyl ether was used as the feed material. The catalyst used was the strongly acid cation-exchange resin (Amberlyst 15). The reaction condition and the result of analyzing the liquid reaction product are shown in the following table.

TABLE 3

Reaction temperature and time
75° C., 2 hr.

| Component | Feed material (mol) | Product (mol) | (Product) - (Feed material) (mol) |
|---|---|---|---|
| Ethylene glycol | 0.590 | 0.562 | −0.028 |
| Diisobutylene | 0.002 | 0.011 | 0.009 |
| Triisobutylene | 0.001 | 0.001 | 0 |
| DBE | 0.055 | 0.002 | −0.053 |
| MBE | 0.220 | 0.301 | 0.081 |

(Note)
DBE: Ethylene glycol di-t-butyl ether
MBE: Ethylene glycol mono-t-butyl ether

EXAMPLE 7

In an autoclave having a 100 ml volume equipped with a stirrer, 5.5 g of sulfonated coal: Dusarit S (manufactured by Activit N. V. Co.), 0.565 mols of ethylene glycol and 0.057 mols of ethylene glycol di-t-butyl ether were put, and a nitrogen gas was introduced thereto. The mixture was subjected to reacting at 60° C. for 4 hours. The pressure was 20 Kg/cm$^2$. The result of analyzing the liquid reaction product is shown in the following table. The ethylene glycol di-t-butyl ether was effectively converted into ethylene glycol mono-t-butyl ether.

TABLE 4

Reaction temperature and time
60° C., 4 hr.

| Component | Feed material (mol) | Product (mol) | (Product) - (Feed material) (mol) |
|---|---|---|---|
| Ethylene glycol | 0.565 | 0.542 | −0.023 |
| Diisobutylene | 0 | 0.002 | 0.002 |
| DBE | 0.057 | 0.031 | −0.026 |
| MBE | 0 | 0.049 | 0.049 |

(Note)
DBE: Ethylene glycol di-t-butyl ether
MBE: Ethylene glycol mono-t-butyl ether

EXAMPLE 8

35.0 g of ethylene glycol, 9.9 g of ethylene glycol di-tert-butyl ether (DBE) and 5.0 g of Amberlyst 15 were charged in a stainless autoclave (100 ml in volume), followed by conducting the reaction at 60° C. In the result of analyzing the reaction product, the changes of the composition (mol %) of each component of ethylene glycol, ethylene glycol mono-tert-butyl ether (MBE) and DBE with the passage of time are tabulated in Table 5. The compositions (mol %) as described in Table 5 are based on the total mols (100 mol %) of ethylene glycol, MBE and DBE in the reaction product in which the butane, butene and polymer of butene formed as by-product are removed.

The results as described in Table 5 show the fact that the amount of each of DBE and ethylene glycol is reduced with the passage of time and the amount of MBE produced is increased with the passage of time. Therefore, it can be appreciated from the results of Table 5 that the reaction of converting DBE into MBE is caused by reacting DBE with ethylene glycol.

TABLE 5

| | Reaction time (hr) | | | | |
|---|---|---|---|---|---|
| Component | 0 | 1 | 2 | 4 | 5 |
| EG (mol %) | 90.8 | 88.6 | 87.4 | 84.0 | 83.8 |
| MBE (mol %) | 0 | 4.8 | 8.8 | 15.4 | 16.0 |
| DBE (mol %) | 9.2 | 6.6 | 3.8 | 0.6 | 0.2 |

(Note)
EG; Ethylene glycol
mol %; based on the total amount (mol) of EG, MBE and DBE.

COMPARATIVE EXAMPLE 11.8 g of isobutylene, 35.0 g of ethylene glycol and 5.0 g of Amberlyst 15 were charged in a stainless autoclave (100 ml in volume), followed by conducting the reaction at 60° C. In the result of analyzing the reaction product in the same procedure as in Example 8, the changes of the composition (mol %) of each component of ethylene glycol, ethylene glycol mono-tert-butyl ether (MBE) and ethylene glycol di-t-butyl ether (DBE) with the passage of time are tabulated in Table 6.

The results of Table 6 show the fact that the amount of DBE is increased with the passage of time and not reduced at all. Further, the amount of the MBE produced was reached to maximum at the reaction time around 3 hours, and then gradually reduced. Therefore, it can be appreciated from the result of Table 6 that the reaction comprising producing MBE by reacting ethylene glycol with isobytylene and then producing DBE by reacting the resulting MBE with isobutylene is successively conducted.

TABLE 6

| | Reaction time (hr) | | | | |
|---|---|---|---|---|---|
| Component | 0 | 1 | 2.5 | 4 | 6 |
| EG (mol %) | 100 | 78.6 | 70.4 | 70.1 | 69.4 |
| MBE (mol %) | 0 | 21.2 | 27.5 | 26.9 | 25.5 |
| DBE (mol %) | 0 | 0.2 | 2.1 | 3.0 | 5.1 |

(Note)
mol %; based on the total amount (mol) of EG, MBE and DBE.

While the invention has been described in detail and with reference to specific embodiments thereof, it will be apparent to one skilled in the art that various changes and modifications can be made therein without departing from the spirit and scope thereof.

What is claimed is:

1. A process for producing ethylene glycol mono-t-butyl ether which comprises contacting a starting mixture consisting of ethylene glycol di-t-butyl ether, and ethylene glycol with a strongly acidic cation-exchange material to react said ethylene glycol di-t-butyl ether with said ethylene glycol in the presence of the strongly acidic cation-exchange material as a catalyst to produce ethylene glycol mono-t-butyl ether.

2. A process for producing ethylene glycol mono-t-butyl ether which comprises contacting a starting mixture consisting of ethylene glycol di-t-butyl ether, ethylene glycol and at least one member selected from the group consisting of ethylene glycol mono-t-butyl ether, diisobutylene, and triisobutylene with a strongly acidic cation-exchange material as a catalyst to react the ethylene glycol di-t-butyl ether in said mixture with the ethylene glycol in said mixture to produce ethylene glycol mono-t-butyl ether.

3. The process according to claim 2, wherein the starting material is a mixture of ethylene glycol di-t-butyl ether, ethylene glycol and ethylene glycol mono-t-butyl ether.

4. The process according to claims 1 or 2, wherein catalyst is a sulfonated material having sulfonic acid groups ($SO_3H$) as functional groups.

5. The process according to claims 1 or 2, wherein the molar ratio of the feed ethylene glycol to the feed ethylene glycol di-t-butyl ether is about 1:0.01 to 1:20.

6. The process according to claims 2 or 3, wherein the molar ratio of the feed ethylene glycol di-t-butyl ether to the feed ethylene glycol mono-t-butyl ether is about 1:0 to 1:20.

7. The process according to claims 2 or 3, wherein the molar ratio of the feed ethylene glycol di-t-butyl ether to the feed ethylene glycol mono-t-butyl ether is about 1:0 to 1:5.

8. The process according to claims 1 or 2, wherein the reaction is carried out at about 30° to 130° C.

9. The process according to claims 1 or 2, wherein the reaction is carried out under atmospheric pressure.

10. The process according to claims 1 or 2, wherein the reaction is carried out under an applied pressure.

11. The process according to claims 1 or 2, wherein the reaction is carried out as a batch process.

12. The process according to claims 1 or 2, wherein the reaction is carried out as a continuous flow process.

13. The process according to claim 12, wherein the linear velocity of the whole feed material in the reaction is at least about 30 cm/hr.

14. A process for producing ethylene glycol mono-t-butyl ether which comprises contacting a starting mixture consisting of (1) ethylene glycol di-t-butyl ether and (2) ethylene glycol and (3), as optional materials, one or more of ethylene glycol mono-t-butyl ether, diisobutylene and triisobutylene, with a strongly acidic cation-exchange material to react said ethylene glycol di-t-butyl ether with said ethylene glycol in the presence of a strongly acidic cation-exchange material as a catalyst to produce ethylene glycol mono-t-butyl ether.

15. The process according to claims 2 or 3, wherein the molar ratio of the feed ethylene glycol di-t-butyl ether to the feed ethylene glycol mono-t-butyl ether is about 1:0 to 1:3.

* * * * *